United States Patent [19]
Garzon et al.

[11] Patent Number: 5,695,624
[45] Date of Patent: Dec. 9, 1997

[54] SOLID STATE OXYGEN SENSOR

[75] Inventors: Fernando H. Garzon, Santa Fe; Eric L. Brosha, Los Alamos, both of N. Mex.

[73] Assignee: The Regents of the Univeristy of California, Alameda, Calif.

[21] Appl. No.: 687,900

[22] Filed: Jul. 29, 1996

Related U.S. Application Data

[63] Continuation-in-part of Ser. No. 381,609, Jan. 30, 1995, Pat. No. 5,543,025.

[51] Int. Cl.$^6$ .................................................. G01N 27/26
[52] U.S. Cl. ...................... 204/425; 204/421; 204/424; 204/426; 204/431; 204/415
[58] Field of Search ..................................... 204/421, 424, 204/425, 426, 427, 429, 431, 415

[56] References Cited

U.S. PATENT DOCUMENTS

| | | | |
|---|---|---|---|
| 4,710,848 | 12/1987 | Schlechtriemen | 361/280 |
| 4,792,752 | 12/1988 | Schlechtriemen et al. | 324/71.1 |
| 4,931,214 | 6/1990 | Worrell et al. | 252/520 |
| 5,023,153 | 6/1991 | Weppner | 429/40 |
| 5,298,235 | 3/1994 | Worrell et al. | 429/33 |
| 5,332,483 | 7/1994 | Gordon | 429/30 |
| 5,378,345 | 1/1995 | Taylor et al. | 204/424 |
| 5,393,397 | 2/1995 | Fukaya et al. | 204/424 |
| 5,397,443 | 3/1995 | Michaels | 204/59 R |

OTHER PUBLICATIONS

W. Weppner, "Tetragonal zirconia polycrystals—a high performance solid oxygen ion conductor", 52 Solid State Ionics, pp. 15–21 (1992). No Month Available.

*Primary Examiner*—Bruce F. Bell
*Attorney, Agent, or Firm*—Ray G. Wilson

[57] ABSTRACT

A potentiometric oxygen sensor is formed having a logarithmic response to a differential oxygen concentration while operating as a Nernstian-type sensor. Very thin films of mixed conducting oxide materials form electrode services while permitting diffusional oxygen access to the interface between the zirconia electrolyte and the electrode. Diffusion of oxygen through the mixed oxide is not rate-limiting. Metal electrodes are not used so that morphological changes in the electrode structure do not occur during extended operation at elevated temperatures.

4 Claims, 5 Drawing Sheets

SOLID STATE OXYGEN SENSOR

This patent application claims the benefit of U.S. Provisional Application filed Jul. 1, 1996, under Docket No. 84,985 and is a continuation-in-part of patent application Ser. No. 08/381,609, filed Jan. 30, 1995, now U.S. Pat. No. 5,543,025, issued Aug. 6, 1995.

This invention was made with government support under Contract No. W-7405-ENG-36 awarded by the U.S. Department of Energy. The government has certain rights in the invention.

BACKGROUND OF THE INVENTION

This invention relates to oxygen sensors and, more particularly, to solid-state oxygen sensors.

An electrochemical zirconia solid electrolyte oxygen sensor has been used for monitoring oxygen concentration in various applications, such as automobiles, to monitor exhaust gas composition and control air-to-fuel ratio for reducing harmful emission components and improving fuel economy. Solid-state electrochemical zirconia oxygen sensors are divided into two groups: (1) potentiometric or logarithmic air/fuel sensors; and (2) amperometric or linear air/fuel sensors. Potentiometric sensors are ideally suited to monitor the air-to-fuel ratio close to the complete combustion stoichiometry—a value of about 14.8 to 1 by volume. The potentiometric sensor is not very sensitive to changes in oxygen partial pressure away from this point because of the logarithmic dependence of the EMF on the oxygen partial pressure, but it does provide an output over a wide range of oxygen partial pressures.

It is advantageous to operate gasoline power piston engines with excess oxygen to improve fuel economy and reduce hydrocarbon emissions. To maintain stable combustion away from stoichiometry and enable engines to operate in the excess oxygen (lean burn) region, several limiting-current amperometric sensors have been reported. These sensors typically show reproducible limiting current plateaus with an applied voltage caused by gas diffusion overpotential at the cathode. The sensor current plateau is generally linearly proportional to the concentration of oxygen in the external environment and the oxygen concentration. These characteristics are obtained by limiting the diffusion of oxygen through a gas diffusion barrier.

Two types of gas diffusion barriers are currently being evaluated: (1) a cavity with a small diffusion diffusion hole; and (2) a porous ceramic layer on the cathode to limit the oxygen transfer rate from the ambient gas. The aperture-type is relatively difficult to manufacture and requires that the aperture remain unplugged. The porous-type is easy to manufacture, but control of the porosity is difficult and the ceramic may provide a changing pore morphology over time.

W. Weppner, "Tetragonal Zirconia Polycrystals—A High Performance Solid Oxygen Ion Conductor," Solid State Ionics 52, 15–21 (1992), suggests that a solid mixed oxygen ion and electronic conductor might be tried to replace an aperture, where the material has a suitable diffusion constant for oxygen. However, there is no teaching about acceptable materials and design parameters for use with solid state electrolytes, e.g., tetragonal zirconia polycrystals (TZP) or cubic stabilized zirconia (CSZ), which are both forms of yttria-doped zirconia.

A potentiometric oxygen sensor with logarithmic characteristics may be formed with an oxygen ion solid state electrolyte with two electrodes that are physically isolated from each other by a gas impermeable separator that is typically the solid electrolyte material itself. A known oxygen concentration is then flowed over one electrode and a sample gas with an unknown oxygen concentration is flowed over the other electrode. The difference in oxygen concentration at the two different surfaces produces a chemical potential gradient between the two electrodes, with a resulting electrochemical potential difference between the two electrodes.

This potentiometric form of sensor is a "Nernstian" type of sensor that obeys Faraday's law:

$$E=(RT/4F)1N(P''O_2/P'O_2)$$

where E is the output voltage of the device, R is the universal gas constant, F is Faraday's constant, $P''O_2$ and $P'O_2$ are the oxygen partial pressures at each electrode and T is the operating temperature in degrees Kelvin.

Typical potentiometric sensors use platinum metal for the electrodes. The metal electrodes provide electrons for the oxygen reduction and oxygen ion oxidation reactions occurring on both electrode structures that establish the device potential. For these reactions to occur on electrodes with limited oxygen diffusivity, the gas needs to be in contact with the solid electrolyte, the metal electrode, and the gas phase. A three phase contact area is essential for the operation of solid electrolyte based oxygen sensors and is obtained by the use of a porous metal electrode. A thick dense platinum metal electrode is not suitable as the platinum metal blocks the transport of oxygen to the metal-solid electrolyte interface where charge transfer occurs.

The use of porous metal electrodes has serious operating temperature and lifetime limitations. The maximum operating temperature and longevity of platinum electrode-zirconia-based oxygen sensors is dictated by the sintering and loss of electrical connectivity of the platinum metal electrodes. After exposures to temperatures above 800° C., significant recrystallization and grain growth occur, causing a loss of electrode three phase contact area. The loss of effective electrode contact area eventually renders the sensor unresponsive to rapid changes in oxygen concentrations in the sample gas.

In accordance with the present invention, suitable solid mixed oxygen ion and electronic conductors are provided for use in potentiometric and amperometric oxygen sensors.

Accordingly, it is an object of the present invention to provide materials as solid mixed oxygen ion and electronic conductors for use in a solid-state oxygen sensor.

Another object of the present invention is to determine suitable operating parameters for oxygen sensors with solid oxygen ion and electronic conductors to provide suitable sensitivity.

One other object of the present invention is to provide a potentiometric oxygen sensor that does not lose oxygen/electron charge transfer contact area under high temperature operating conditions.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus of this invention may comprise a potentiometric solid-state oxygen sensor. The oxygen sensor is formed from a solid oxide electrolyte substrate with a mixed solid oxygen ion and electronic conductor on each surface of the solid oxide electrolyte. Each mixed conductor has a thickness wherein oxygen diffusion through the mixed conductor does not limit the rates of oxygen reduction and oxidation adjacent the surfaces of the solid oxide electrolyte while the mixed oxide conductor forms an electrically conductive layer on each surface of the solid oxide electrolyte. A suitable mixed conductor is a perovskite mixed conductor, e.g., a lanthanum-containing perovskite mixed conductor or a zirconia-containing fluorite mixed conductor, e.g., terbia-doped zirconia. The solid oxide electrolyte is preferably a stabilized zirconia, e.g., yttria-doped zirconia. However ceria-based oxide electrolytes or perovskite oxide ion solid electolytes may also be used

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE INVENTION

Solid state oxygen sensors that use zirconia for an electrolyte are based on the electrochemical oxygen pumping of a zirconia electrolyte. In one application, amperometric sensors show reproducible limiting current plateaus with an applied voltage caused by the gas diffusion overpotential at the cathode. The sensor plateau is linearly proportional to the concentration of oxygen in the external environment. This phenomenon occurs because the diffusion of the oxygen through a gas diffusion barrier, e.g., a pinhole barrier or a porous layer, as used in prior art devices, is the rate-determining step. In accordance with the present invention, the diffusion barrier is formed with a mixed electronic and oxygen ion-conducting solid membrane. The diffusion of oxygen through the mixed conducting solid material is much slower than through a gas and improved sensor performance is obtained without the problems of the prior art. Further, the mixed conductor is also a very good electronic conductor and acts as a cathode with the charge transfer reaction occurring across the entire mixed conductor and electrolyte interfacial area. While this basic concept has been suggested, we have found particular mixed conductors and operating parameters that provide a linear relationship between the voltage at a limiting current and oxygen concentration in an applied gas.

In another application of zirconia electrolytes, a potentiometric oxygen sensor is formed having a logarithmic response to a differential oxygen concentration while operating as a Nernstian-type sensor. In this application, very thin films of mixed oxide materials form electrode surfaces while permitting gas phase access to the interface between the zirconia electrolyte and the mixed oxide electrode. The thickness of the mixed oxide electrode is selected so that diffusion of oxygen through the mixed oxide is not reaction rate-limiting. Metal electrodes are not used so that morphological changes in the electrode structure do not occur during extended operation at elevated temperatures.

Figure 1:
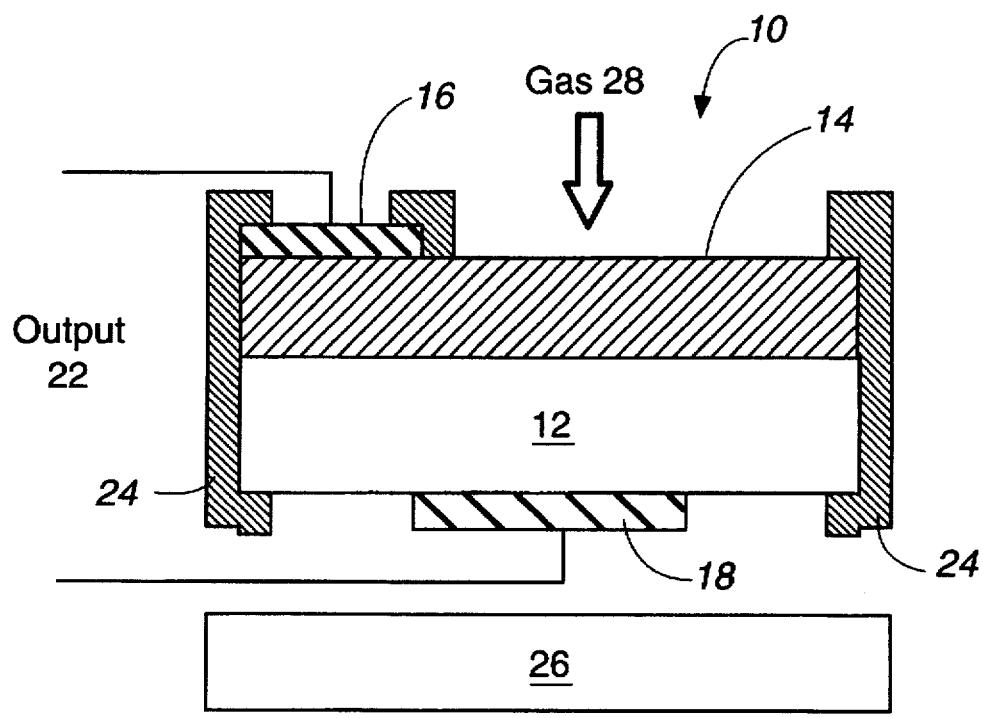
FIG. 1 is a cross-sectional view of one embodiment of an oxygen sensor according to the present invention.
Figure 2:
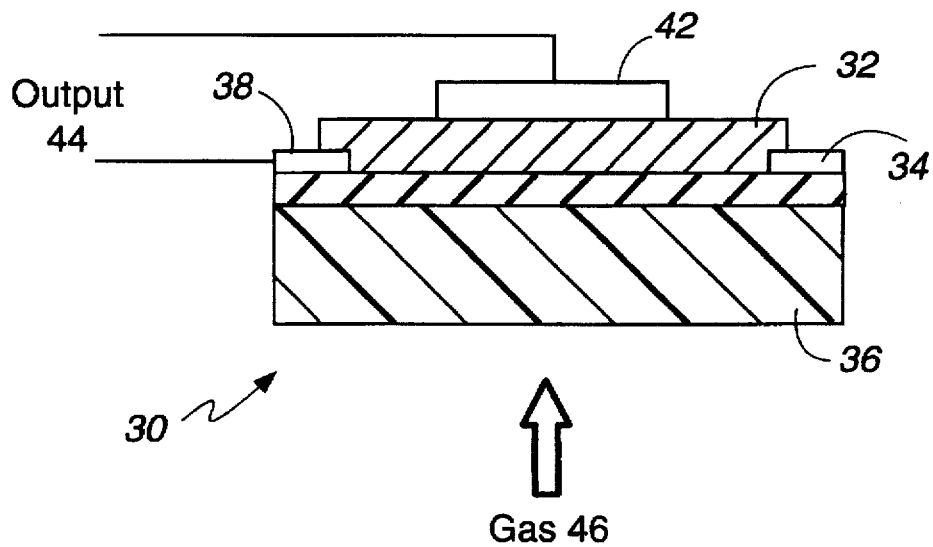
FIG. 2 is a cross-sectional view of a second embodiment of an oxygen sensor according to the present invention.

FIGS. 1 and 2 show cross-sections of exemplary amperometric, or linear, solid-state oxygen sensors according to one aspect of our invention. FIG. 1 depicts oxygen sensor 10 having a solid electrolyte 12 substrate with an overlying membrane of a mixed conductor 14. Electrode pads 16, 18, e.g., Pt electrodes, are in contact with mixed conductor 14 and electrolyte 12, respectively. The application of a gas 28 that contains oxygen will produce a limiting current output 22 as a dc potential is applied across the sensor, where the limiting current is linearly related to the concentration of oxygen in gas 28. In some instances, heater 26 may be provided to maintain an adequate diffusion coefficient in the mixed conducting layer 14.

Electrolyte 12 was formed from yttria-doped zirconia substrates obtained from A. C. Rochester and Enprotech respectively. Typical thicknesses of the yttria-doped zirconia substrates were 0.07 cm and 0.05 cm. The mixed conductors were formed from hot-pressed targets of $La_{0.84}Sr_{0.16}MnO_3$ (LSMO) and $La_{0.8}Sr_{0.2}CoO_3$ (LSCO) (Seattle Specialty Ceramics). The mixed conductors were deposited by a 90° off-axis radio-frequency (rf) magnetron sputtering technique. The depositions were done at an rf power of 100 W at a temperature of 700° C. Pt electrode pads 16, 18 were applied by sputtering. Glass seals 24 were applied to minimize electrochemical oxygen leakage.

FIG. 2 depicts a cross-sectional view of an alternate thin film embodiment of an oxygen sensor 30. Sensor 30 includes mixed conductor 34 deposited on a porous substrate 36, which may be $Al_2O_3$, and a film of an electrolyte 32 deposited on the mixed conductor layer. Electrode pads 38, 42 are suitably deposited on mixed conductor 34 and electrolyte 32, respectively. Gas 46 containing an oxygen content is sampled through porous substrate 36 and a current output 44 is provided. It will be understood that the position of electrolyte 32 and mixed conductor 34 may be reversed, whereby gas 46 is incident directly on mixed conductor 34.

Figure 3:
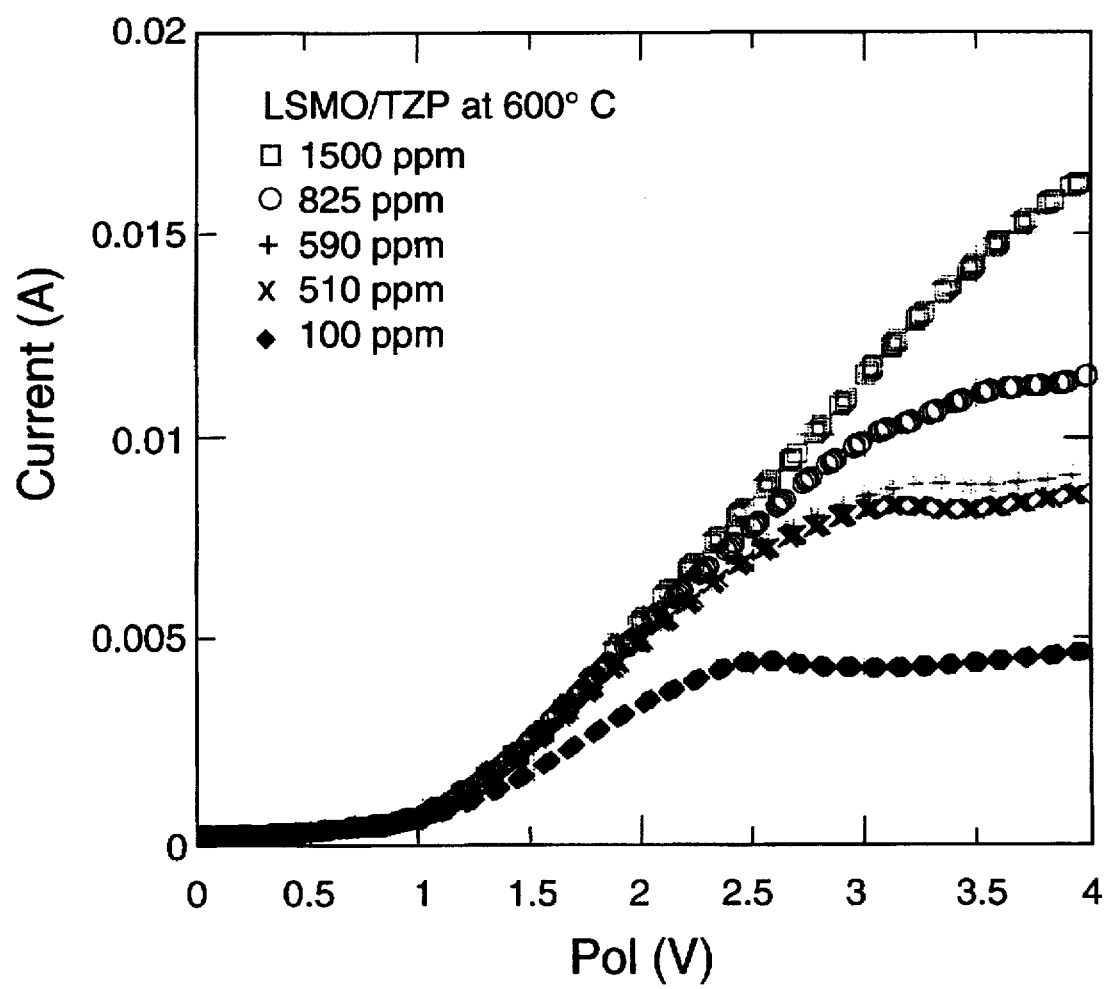
FIG. 3 graphically illustrates sensor i-V characteristics with limiting current plateaus at various oxygen concentrations.

FIG. 3 graphically illustrates the sensor i-V characteristics with limiting current plateaus at various oxygen concentrations. FIG. 3 is specifically for a LSMO mixed conductor on a yttria-doped zirconia substrate operating at 600° C. The gas mixture was oxygen and argon with controlled oxygen pressures, ranging from 0.01 to 20%. The oxygen partial pressure was fixed and measured using an Ametek oxygen analyzer. The sensors were connected to a Solartron 1286 Electrochemical Interface potentiostat and polarization potentials were incremented from 0–4 volts and the corresponding electrochemical current was recorded for each device. A set of data was taken at different furnace temperatures.

The i-V characteristic curves of a typical linear sensor according to our invention, exemplified by FIG. 3, has four regimes that represent different electroactive processes. In the beginning, the current increases exponentially with the applied voltage, perhaps due to a charge transfer reaction at the mixed conductor and solid electrolyte interface. The second regime shows an ohmic behavior in which the output current increases with increasing applied voltage due to the combined ionic transport in the mixed conductor and the solid electrolyte. Because the mixed conductors have electronic and oxygen ion conductivities that are several orders of magnitude higher than those of the solid electrolyte, the slopes are predominantly caused by the ohmic behavior of the solid electrolyte.

The third regime features the limiting current plateau, which is determined by the gas diffusion through the mixed conductor diffusion barrier. This current can be described using the following relationship:

$$i_l = \frac{4FD_{O_2}SC_{O_2}(0)}{L} \quad (1)$$

Where $i_l$, F, $D_{O_2}$, S, $C_{O_2}(0)$, and L are the limiting current, the Faraday constant, the oxygen diffusion coefficient through the mixed conductor at a given temperature, the surface area of the mixed conductor (diffusion barrier), the oxygen concentration in the ambient gas, and the thickness of the mixed conductor, respectively.

In the limiting-current plateau region, the rate determining step is based on the diffusion of oxygen atoms through the lattice of the mixed conductors. Since the electronic conductivity of mixed conductors is so high, the gradient of electrical potential is very small. Therefore, oxygen transport through these materials occurs only due to an oxygen chemical potential gradient. FIG. 3 shows that the limiting current plateaus have a slight slope with increasing applied voltage, believed to be caused by a mixture of ohmic current proportional to the applied voltage and by a current based on the diffusion restriction of atomic oxygen through the mixed conductors. The ohmic current is caused by electrochemical leakage around the solid electrolyte/mixed conductor interface.

Another observation of i-V characteristics of the sensors is the observation of a peak at the beginning of the limiting-current plateau. This peak is observed only at the current plateaus for low oxygen concentrations. This may be caused by a change in the stoichiometry of the metal oxide before reaching the limiting-current plateau.

The fourth regime is the i-V characteristic beyond the limiting current plateau. This region is caused by the electrochemical decomposition of the electrolyte and is most dramatic at the highest operating temperatures.

Figure 4:
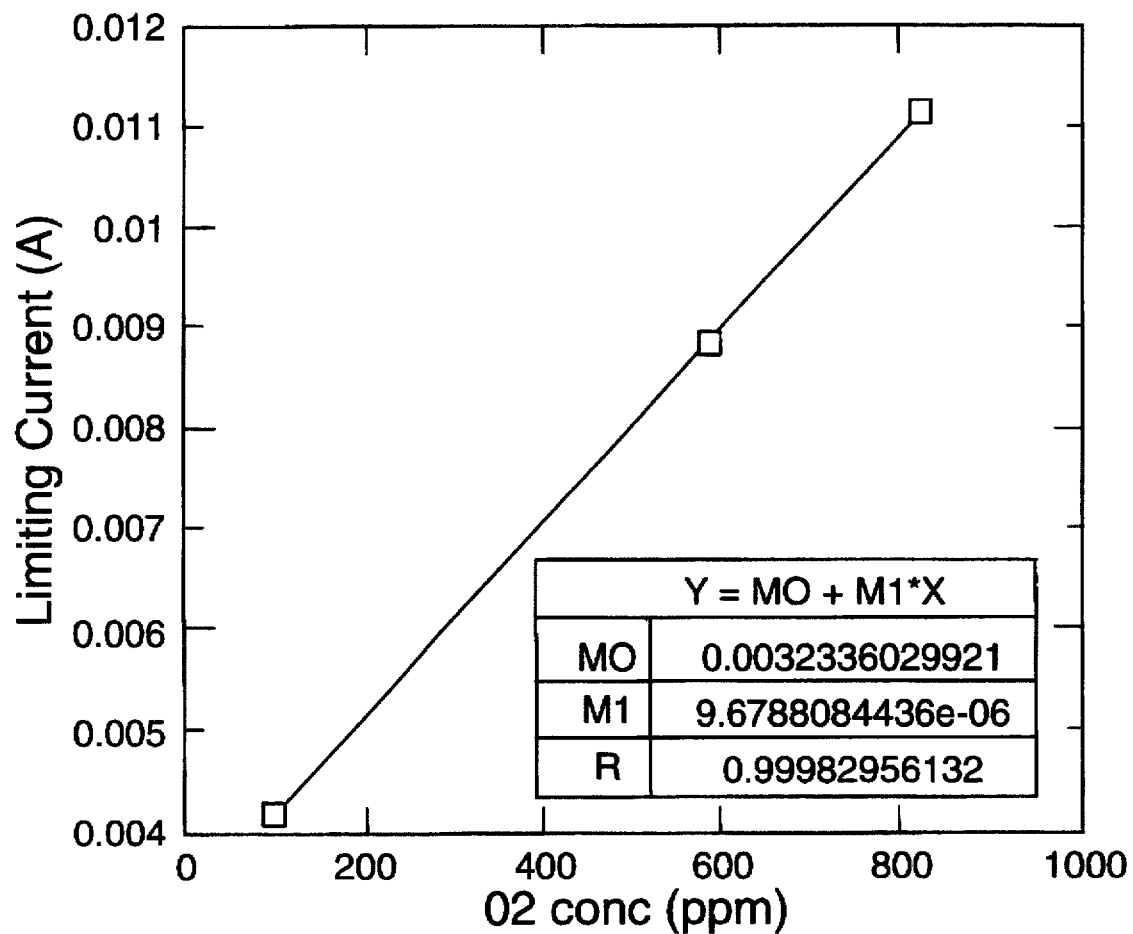
FIG. 4 graphically depicts the linear response of a sensor having the i-V characteristics shown in FIG. 3.

FIG. 4 demonstrates the linear response of the sensor having the i-V characteristic curves depicted. The best fit curve is given by Y=M0+M1*X, where Y is the limiting current value in amperes, X is the oxygen concentration in ppm, M0 is the Y intercept and M1 is the slope. A steep slope is needed for very sensitive instruments, where a shallower slope is desired for instruments that cover a wider range of oxygen concentration. A measure of the linearity of the data is the correlation factor R that correlates the data to the linear relationship. A perfect fit would be R=1. A suitable linear relationship for an oxygen sensor is given by R greater than about 0.9.

Table A–G below present exemplary results showing the linear relationship between plateau currents and oxygen concentration using perovskite mixed conductors of LSMO and LSCO; solid electrolytes of yttria-doped zirconia; thin films of mixed conductors and electrolyte on an alumina substrate; and a mixed conductor on an alternate, yttria-doped zirconia electrolyte (CeraFlex). The linear relationships were explored at various temperatures (600° C., 700° C., and 800° C.) and film thicknesses as noted.

TABLE A

LSMO on Yttria-doped Zirconia

| T° C. | t (μm) | 1 | 1.6 |
|---|---|---|---|
| 600 | M0 | 0.00323 | 0.002198 |
|  | M1 | 0.96788e − 05 | 0.79805e − 05 |
|  | R | 0.99983 | 0.99979 |
| 700 | M0 | 0.00611 |  |
|  | M1 | 1.22234e − 05 |  |
|  | R | 0.99976 |  |
| 800 | M0 | 0.01026 |  |
|  | M1 | 1.25656e − 05 |  |
|  | R | 0.99974 |  |

TABLE B

LSMO on Yttria-doped Zirconia

| T° C. | t (μm) | .49 | .6705 | .921 |
|---|---|---|---|---|
| 600 | M0 | 0.00324 | 0.00382 | 0.00396 |
|  | M1 | .7938e − 05 | 1.0126e − 05 | 1.1115e − 05 |
|  | R | 0.99663 | 0.9867 | 0.9989 |
| 700 | M0 | 0.00273 |  | 0.00942 |
|  | M1 | 1.3752e − 05 |  | 1.3689e − 05 |
|  | R | 0.9938 |  | 0.99994 |
| 800 | M0 | 0.00213 |  | 0.01479 |
|  | M1 | 1.4497e − 05 |  | 2.2192e − 05 |
|  | R | 0.99216 |  | 0.9985 |

TABLE C

LSCO on Yttria-doped Zirconia

| T° C. | t (μm) | <.20 |
|---|---|---|
| 650 | M0 | 0.0002 |
|  | M1 | .7163e − 05 |
|  | R | 0.9994 |
| 750 | M0 | 0.00015 |
|  | M1 | .8446e − 05 |
|  | R | 0.9964 |

TABLE D

LSCO on Yttria-doped Zirconia

| T° C. | t (μm) | .695 |
|---|---|---|
| 600 | M0 | 0.00525 |
|  | M1 | 1.0807E − 05 |
|  | R | 0.9999 |
| 700 | M0 | 0.00776 |
|  | M1 | 1.2148E − 05 |
|  | R | 0.9996 |

TABLE E

LSCO on Yttria-doped Zirconia

| T° C. | t (μm) | 1.7 |
|---|---|---|
| 600 | M0 | 0.00102 |
|  | M1 | .3388e − 05 |
|  | R | 0.966 |
| 700 | M0 | 0.00055 |
|  | M1 | .7042e − 05 |
|  | R | 0.995 |

TABLE F

LSMO on CeraFlex

| T° C. | t (μm) | 1 |
|---|---|---|
| 600 | M0 | 3.7187 |
| | M1 | 0.00768 |
| | R | 0.9998 |

TABLE G

Thin Film Yttria-doped Zirconia on LSMO - Al₂O₃ Support

| T° C. | t (μm) | 6.7 ($t_{LSMO}$)/10 ($t_{YSZ}$) | 6.7 ($t_{LSMO}$)/10 ($t_{YSZ}$) Inverted |
|---|---|---|---|
| 600 | M0 | 0.00455 | 0.00407 |
| | M1 | .2891e − 05 | .2663e − 05 |
| | R | 0.9948 | 0.9899 |

In addition to lanthanum-containing perovskite mixed conductors, linear oxygen sensing has also been obtained from a zirconia-containing fluorite mixed conductor, $Zr_{0.62}Tb_{0.30}Y_{0.08}O_{3-y}$ (Tb-YSZ), as shown in Table H.

TABLE H

Tb-YSZ Diffusion Barrier on Yttria-doped Zirconia

| T° C. | t (μm) | 100 |
|---|---|---|
| 740 | M0 | 0.0000443 |
| | M1 | .05964e − 05 |
| | R | 0.9978 |

The dynamic range for these limiting current solid state oxygen sensors is determined by a number of device parameters. The range of oxygen concentration detected is larger with higher temperatures because of higher conductivity of the solid electrolyte with increasing temperature. The range can be increased significantly by using thin-film technology to form a multilayer thin-film sensor on a porous substrate (FIG. 2 and Table G) so that oxygen is pumped through the device and passed through to the ambient gas environment.

The oxygen sensor response can be further optimized by tailoring the thickness of the barrier layer for the oxygen concentration range that is desired. The mixed conductors used as diffusion barriers for our exemplary oxygen sensors had a relatively high oxygen diffusion coefficient. The high mobility of oxygen through the mixed conductor diffusion barrier limits the sensor's detection range at the currently used thicknesses.

To increase the range of the detection range, the thickness of the diffusion barrier layer can also be increased with currently available thick film technology such as screen printing. A LSMO mixed conductor was mixed with glycerin to form an ink that was screen printed on a substrate. The performance of the sensor is shown in Table I. Table I is not directly comparable to the other Tables since oxygen concentration is determined in % partial pressure rather than in parts-per-million (PPM). However, the sensitivity of the device, as measured by the slope, M1, is quite high compared to thinner film devices.

TABLE I

Glycerin-deposited LSMO on Yttria-doped Zirconia

| T° C. | t (μm) | 100 |
|---|---|---|
| 700 | M0 | 0.00011459 |
| | M1 | 34.701e − 05 |
| | R | 0.99996 |

Figure 5:
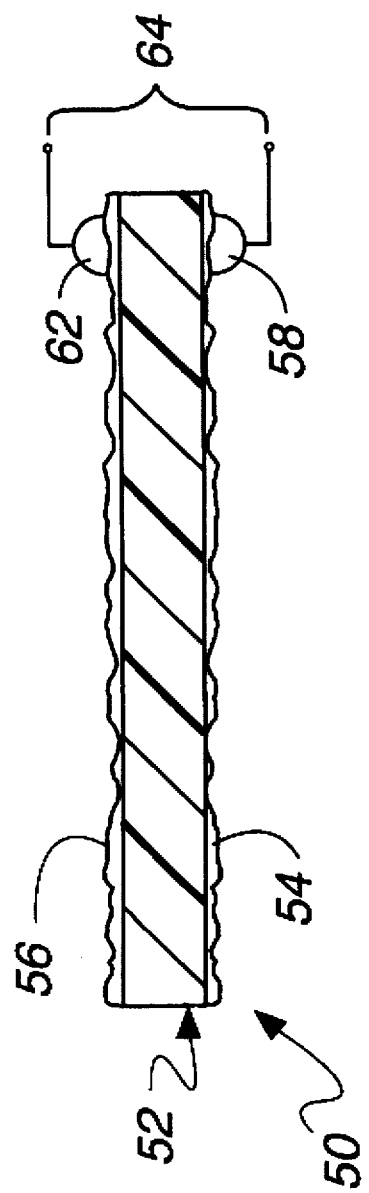
FIG. 5 is a cross-section of a potentiometric oxygen sensor according to one embodiment of the present invention.

Referring now to FIG. 5, there is shown in cross-section a potentiometric-response oxygen sensor 50 without metal electrode surfaces, i.e., a sensor having a logarithmic response in accordance with another application of our invention applying mixed oxide films to oxygen sensors. Solid state zirconia electrolyte 52 defines opposed surfaces on which are deposited mixed oxide films 54 and 56. To facilitate connecting to an external electrical circuit 64, metal pads 58, 62 are conventionally placed on the mixed oxide films. Metal pads 58, 62 do not cover any significant area of mixed oxide films 54, 56 and may be formed of any compatible conducting material, e.g., gold or silver.

Mixed oxide films 54, 56 may be formed by a sputtering technique, as discussed above, so that the deposited materials are dense and have a stable morphology. The deposited material has a high oxygen diffusivity and the deposition thickness is thin enough that oxygen diffusion to the electrolyte surface is not rate limiting. Porous structure that is unstable at high temperatures is eliminated. It will be appreciated that a completely solid film of mixed conductors 54 and 56 is not required; sufficient material is deposited to provide generally electrically contiguous films.

The maximum thickness of films 54, 56 is a function of the desired response time and the oxygen chemical diffusion coefficient of the selected mixed conductor at the operating temperature of the device. For example, the diffusion coefficient D of $La_{0.35}Sr_{0.15}MnO_3$ at 800° C. is about $1\times10^{-8}$ cm²/sec. A maximum film thickness x (the diffusion distance) is determined by $x=\sqrt{2Dt}$, where t is the time required for diffusion, i.e., the sensor response time. For the sensor to equilibrate to a change in ambient oxygen pressure within 1 sec., the electrode thickness is on the order of 1.4 μm. Thinner films would decrease the response time, while thicker films would increase the response time. The mixed conductors discussed above are refractory compounds that exhibit high melting points and metal ion mobilities that are less than platinum metal. The mixed conductor electrodes also have strong ionic bonding between the electrolyte and the mixed oxide for improved adherence over platinum metal electrodes.

A prior art oxygen sensor is described in Fukaya et al., U.S. Pat. No. 5,393,397, where an oxygen sensor is taught with a "sandwich" structure of a porous mixed conductor film with a porous platinum metal electrode overcoat on each surface. The electrode films are thick porous layers (e.g., lanthanum strontium cobalt oxide) and require an extensive overcoat of platinum metal for good performance. Our invention uses a thin continuous film of mixed conductor that is only physically contacted by a dense platinum contact patch or pressed metal mesh current collector, i.e., a limited area contact that does not contribute to the electrochemical reactions that govern the response of the sensor. The operating conditions taught by Fukaya et al. are for low temperature applications below 700° C. Under operation at high temperatures, Fukaya would be expected to suffer significant performance loss as the platinum electrode area undergoes recrystallization and grain growth with a corresponding loss of contact area.

Figure 6:
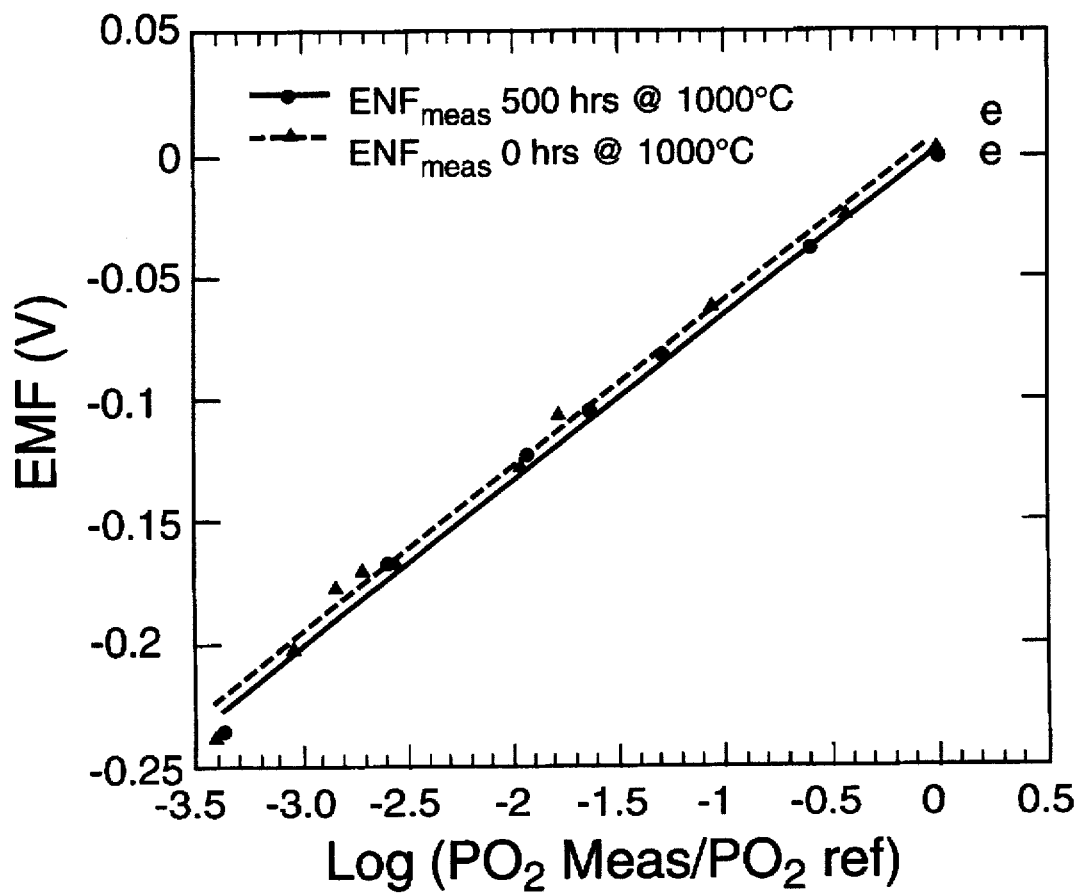
FIG. 6 graphically depicts the stable operating performance of a potentiometric oxygen sensor according to the present invention over 500 hours at 1000° C.

The mixed oxide Nernstian-type oxygen sensor described above has a greatly enhanced thermal stability over conventional platinum-type potentiometric oxygen sensors. FIG. 6 graphically depicts the stable response of a Nernstian-type oxygen sensor having mixed oxide electrodes of $La_{0.84}Sr_{0.16}MnO_3$. It is readily apparent from the figure that there is no discernible change in the response characteristics of the sensor even after 500 hours of operation at 1000° C.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A potentiometric solid-state sensor having an output signal logarithmically related to the concentration of oxygen in an unknown gas stream, said sensor comprising:

a solid oxide electrolyte defining a pair of opposed surfaces and forming a barrier therebetween that is impermeable by said gas stream;

a mixed conductor electrode formed from a mixed conductor selected from the group consisting of lanthanum-containing perovskite and -zirconia-containing fluorite disposed on each one of said opposed surfaces to a thickness wherein the thickness of said mixed conductor electrode does not limit the reaction rate of oxygen to interfaces of said solid oxide electrolyte and said mixed conductor electrode and wherein said mixed conductor electrode forms an electrically conductive layer; and metallic electrodes contacting a small portion of each said electrically conductive layer for transporting a current therebetween, wherein one said mixed conductor electrode is exposed to said unknown gas stream and another said mixed electrode is exposed to a reference gas stream with a known concentration of oxygen so that an output voltage is generated therebetween.

2. A potentiometric solid-state sensor according to claim 1, wherein said thickness of said mixed conductor electrode is less than a value determined from $x=\sqrt{2Dt}$, where x is said thickness of said mixed conductor electrode D is a coefficient of diffusion for said mixed conductor electrode at a selected operating temperature, and t is a desired response time for said sensor.

3. A potentiometric solid-state sensor having an output signal logarithmically related to the concentration of oxygen in an unknown gas stream, said sensor consisting essentially of:

a solid oxide electrolyte defining a pair of opposed surfaces and forming a barrier therebetween that is impermeable by said gas stream;

a mixed conductor electrode formed from a mixed conductor selected from the group consisting of lanthanum-containing perovskite and -zirconia-containing fluorite disposed on each one of said opposed surfaces to a thickness wherein the thickness of said mixed conductor electrode does not limit the reaction rate of oxygen to interfaces of said solid oxide electrolyte and said mixed conductor electrode and wherein said mixed conductor electrode forms an electrically conductive layer; and metallic electrodes contacting a small portion of each said electrically conductive layer for transporting a current therebetween, wherein one said mixed conductor electrode is exposed to said unknown gas stream and another said mixed electrode is exposed to a reference gas stream with a known concentration of oxygen so that an output voltage is generated therebetween.

4. A potentiometric solid-state sensor according to claim 3, wherein said thickness of said mixed conductor electrode is less than a value determined from $x=\sqrt{2Dt}$, where x is said thickness of said mixed conductor electrode, D is a coefficient of diffusion for said mixed conductor electrode at a selected operating temperature, and t is a desired response time for said sensor.

* * * * *